(12) United States Patent
Gärber (10) Patent No.: US 9,730,607 B2
(45) Date of Patent: Aug. 15, 2017

(54) ELECTRICAL IMPEDANCE TOMOGRAPHY DEVICE AND PROCESS

(75) Inventor: Yvo Gärber, Kastorf (DE)

(73) Assignee: DRÄGERWERK AG & CO. KGaA, Lübeck (DE)

( * ) Notice: Subject to any disclaimer, the term of this patent is extended or adjusted under 35 U.S.C. 154(b) by 1214 days.

(21) Appl. No.: 13/494,585

(22) Filed: Jun. 12, 2012

(65) Prior Publication Data

US 2013/0002264 A1 Jan. 3, 2013

(30) Foreign Application Priority Data

Jul. 2, 2011 (DE) ........................ 10 2011 106 405

(51) Int. Cl.
  *A61B 5/00* (2006.01)
  *A61B 5/053* (2006.01)
  *A61B 5/08* (2006.01)

(52) U.S. Cl.
  CPC .............. *A61B 5/0536* (2013.01); *A61B 5/08* (2013.01)

(58) Field of Classification Search
  CPC ................................ A61B 5/0536; A61B 5/08
  See application file for complete search history.

(56) References Cited

U.S. PATENT DOCUMENTS

| 6,236,886 B1* | 5/2001 | Cherepenin | A61B 5/0536 600/547 |
| 2003/0093004 A1* | 5/2003 | Sosa | A61B 5/04 600/544 |
| 2003/0216630 A1* | 11/2003 | Jersey-Willuhn | A61B 5/0536 600/407 |
| 2006/0085049 A1 | 4/2006 | Cory et al. | |
| 2007/0010758 A1* | 1/2007 | Matthiessen | A61B 5/0536 600/547 |

FOREIGN PATENT DOCUMENTS

| DE | 60017384 T2 | 3/2006 |
| EP | 1 000 580 A1 | 5/2000 |
| WO | 2007/089062 A1 | 8/2007 |

OTHER PUBLICATIONS

Pulletz S, van Genderingen HR, Schmitz G, Zick G, Schadler D, Scholz J, Weiler N, Frerichs I: Comparison of different methods to define regions of interest for evaluation of regional lung ventilation by EIT. 2006 Physiol. Meas. 27 S115-S127.*

ZQ Chen. "Reconstruction algorithms for electrical impedance tomography." Doctor of Philosophy thesis, Department of Electrical and Computer Engineering, University of Wollongong, 1990. http://ro.uow.edu.au/theses/1348. Accessed Nov. 28, 2016.*

(Continued)

*Primary Examiner* — Amanda Lauritzen Moher
(74) *Attorney, Agent, or Firm* — McGlew and Tuttle, P.C.

(57) ABSTRACT

An EIT device has a plurality of electrodes (4) that can be arranged on a body in order to reconstruct the impedance distribution of the body with a reconstruction algorithm. The control unit (10) of the EIT device is set up by suitable programming to continuously determine at least one property (e1, . . . , eM) each from the measured signals (U1, . . . , UM) of all measuring channels and to correct measured signals of the measuring channels on the basis of the properties or to adapt the reconstruction algorithm on the basis of the properties.

13 Claims, 7 Drawing Sheets

(56) References Cited

OTHER PUBLICATIONS

Babaeizadeh, S.; Brooks, D.H.: Imaging Error from Mislocation of Surface Sensors: Sensitivity, Detection, and Estimate Correction, with Application to EIT. In: Acoustics, Speech and Signal Processing, 2006. ICASSP 2006 Proceedings. 2006 IEEE International Conference on, vol. II, Jul. 24, 2006, 585-588.—ISSN 1520-6149.
Hahn et al., Systematic errors of EIT systems determined by easily-scalable resistive phantoms, Physiological Measurements, Jun. 1, 2008, pp. 163-172, vol. 29, IOP Publishing, Bristol.
Promovych, Measurement Systematic Error Decreasing Under Electrical Impedance Tomography, Modern Problems of Radio Engineering, Telecommunications and Computer Science (TCSET), 2010 International conference on, 2010, IEEE, p. 349.

\* cited by examiner

ELECTRICAL IMPEDANCE TOMOGRAPHY DEVICE AND PROCESS

CROSS REFERENCE TO RELATED APPLICATIONS

This application claims the benefit of priority under 35 U.S.C. §119 of German Patent Application DE 10 2011 106 405.6 filed Jul. 2, 2011, the entire contents of which are incorporated herein by reference.

FIELD OF THE INVENTION

The present invention pertains to an electrical impedance tomography device with a plurality of electrodes, which can be arranged on a body, with control and measuring circuits to feed alternating current or alternating voltage to the electrodes and to receive voltage or current signals received from the electrodes as measured signals, and with a control unit, which is connected to the control and measuring circuits and is set up by suitable programming to supply one electrode pair each with an alternating current or with an alternating voltage, to receive the voltage signal or current signal of each electrode pair from all other electrode pairs as a measured signal of a measuring channel and to have the feeding electrode pair to successively pass through the plurality of electrodes in order to thus receive and process measured signals ($U_1, \ldots, U_M$) in a plurality of M measuring channels ($K_1, \ldots, K_M$) in order to reconstruct therefrom the impedance distribution of the body in the electrode plane with a reconstruction algorithm.

BACKGROUND OF THE INVENTION

Such an electrical impedance tomography device (EIT device) is known, for example, from EP 1 000 580 A1, which is used to record an "electrical impedance tomography image" of a cross section of the body of a patient.

Electrical impedance tomography is a process for reconstructing impedance distributions or impedance changes relative to a reference distribution in electrically conductive bodies. A plurality of electrodes are applied for this to the conductive surface of the body being examined, and the control unit, usually a digital signal processor, ensures that a pair each of (preferably) adjacent electrodes is supplied consecutively with an electric alternating voltage (for example, 5 mA at 50 kHz) and the electric voltages are detected at the remaining electrodes and sent to the control unit. Due to the combination of the measured voltage values during the consecutive rotating current feeds, the impedance distribution or the change thereof relative to a reference distribution can be reconstructed with suitable algorithms. A ring-shaped, equidistant arrangement of 16 electrodes, which can be placed, for example, around the body of a patient with a belt, is used in typical applications. Alternating current is fed into two adjacent electrodes each and the voltages are measured between the remaining currentless electrode pairs and received by the control unit. A plurality of measured voltage values, from which a two-dimensional tomogram of the impedance distribution relative to a reference in the electrode plane can be reconstructed, are obtained by rotating the current feed points.

Figure 1:
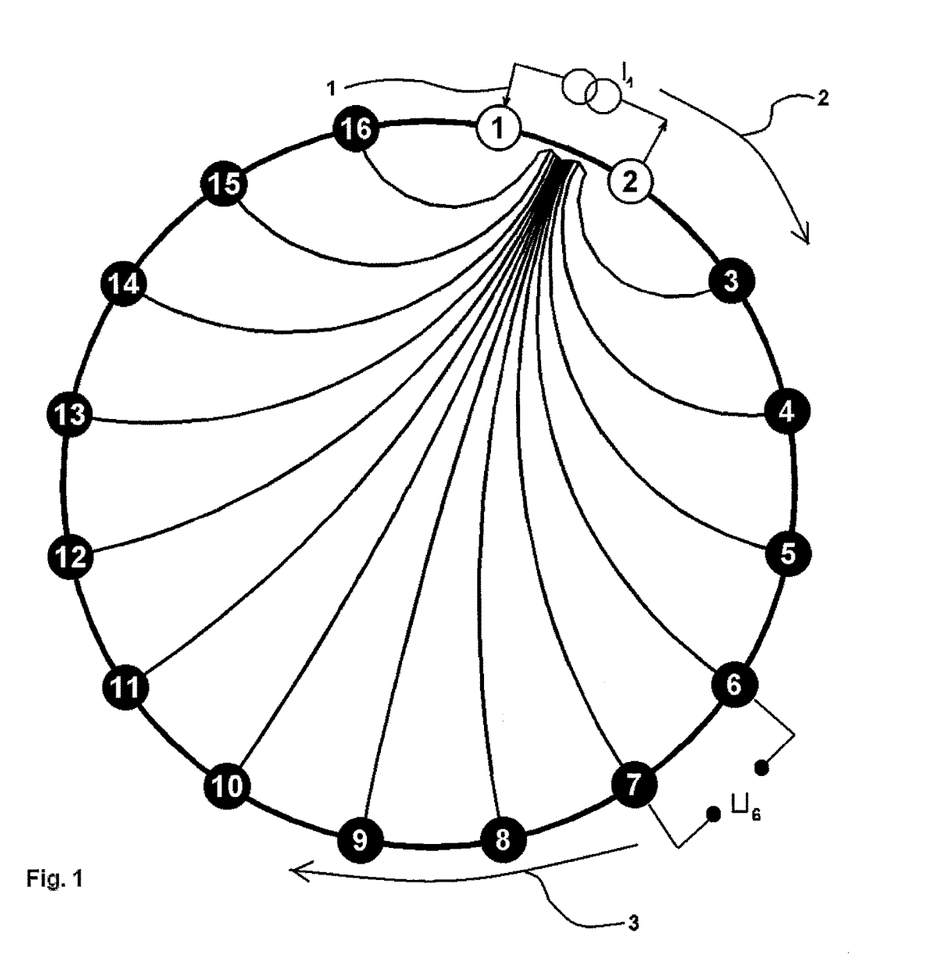
FIG. 1 is a schematic view of data acquisition for a 16-electrode EIT system with equipotential lines shown between current feed electrode pair and voltage-measuring electrodes.

Electrical impedance tomography has been increasingly used in medical research. Typical EIT devices use 8, 16 or 32 electrodes for data acquisition, with current (voltage) being fed (applied) to two or more electrodes and the resulting voltage (current) being measured between the remaining electrodes. The first variant shall be considered below. The second variant may be considered analogously by replacing current and voltage as the feed and measured variable. By combining different feeds and measurements, it is possible to generate a signal vector, from which the impedance distribution can be determined by means of a suitable algorithm or the relative change in the impedance distribution relative to a reference value can be determined in the electrode plane in case of a functional EIT (fEIT). The latter is used for the state-dependent fEIT of the thorax, in which N electrodes are arranged in a ring-shaped pattern around the thorax in order to reconstruct from the comparison of the signal vectors in different states of the lungs (e.g., end-inspiratory and end-expiratory states) a tomogram of the ventilation-related relative impedance change, which is an indicator of the regional distribution of the ventilation of the lungs. The components of the signal vector, i.e., the voltages here, are assigned an unambiguous combination of current feed electrode pair and voltage-measuring electrode pair. This combination is called a channel or measuring channel here. The so-called adjacent data acquisition, where current is fed between two adjacent electrodes and the voltages are measured between the remaining adjacent electrode pairs, is frequently used. A total of 16*13=208 measuring channels, see FIG. 1, are obtained here from 16 current feeds and 13 measuring pairs. Based on the reciprocity when transposing current feed and voltage measurement, only 104 of them are linearly independent. The measured voltage value vector, from which a tomogram can be calculated (frame), is formed from the voltage measurements of the channels. The adjacent DAQ mode is characterized by high sensitivity with respect to relative impedance changes, but it has the drawback that very low voltages appear at times, which may contain an error. Greater distances between current feed and/or voltage measurement are more robust in this respect, but sensitivity is, in general, lost.

From a mathematical physical point of view, EIT is an ill-posed, inverse, nonlinear problem. This means that small errors in the measured boundary voltages are manifested in very great errors in the inverse solution, conductivity distribution or impedance distribution and the solution does not in general, always depend on measured erroneous marginal voltages. The ill-posedness persists even in the linearized case of functional thoracic EIT with small changes in the state of the lungs due to ventilation relative to a reference state of the lungs. In case of matrix representation of the reconstruction, this is reflected, in general, by a poor condition of matrices, which describe the relationship between changes in conductivity (or impedance changes) in the interior of the object studied and changes of the measured voltages at the edge of the object studied with known current feed. Mathematical methods, e.g., regularization for cushioning the poor conditions, are therefore used, but this leads to a limitation of the solution space and a reduction of spatial resolution.

A middle-of-the-road approach is typically sought between robustness to measuring errors and resolution. The regularization strength is controlled based on a so-called regularization parameter, which is adapted to the signal-to-noise ratio (SNR) found. Measured values with different noises in the reconstruction process may possibly also be weighted differently with the correlation matrix analogously to a weighted mean value $$\langle x \rangle = (\Sigma x_i / \sigma_i^2)/(\Sigma 1/\sigma_i^2)$$

with $\sigma_i$ as the statistical error of a measured variable $x_i$. The SNR is primarily a device-specific variable, for which the hardware of many EIT systems is optimized. A fixed reconstruction rule, once generated, which takes into account the SNR, e.g., in weighting and/or regularization, is therefore usually used as a reconstruction. This usually suffices for laboratory experiments with fairly constant and idealized environment.

However, the concept of a fixed reconstruction rule often proves to be insufficient in the daily practice of clinical application. It is seen, in particular, that simply taking statistical errors (SNR) into account alone for the reconstruction rule is often not robust enough for the practical clinical application of EIT. With modern electronics and computer technology, noise does not usually prove to be a limiting factor of a successful measurement. The measuring errors, which form marked artifacts in electric impedance tomograms, are mostly of a systematic nature. These systematic measuring errors are caused, e.g., by common mode voltages or inductive crosstalk (capacitive crosstalk can often be properly screened). In addition, these measuring errors often change over time. This exact value of the systematic measuring errors is typically unknown, so that correction of the voltages themselves is usually impossible. Current EIT systems were used to a great deal under laboratory conditions with phantoms or on healthy volunteers, where the relative systematic error component is very small. Therefore, these interferences are not taken into account by the current reconstruction rules in EIT. However, it is often seen in routine clinical practice in patients with critical lung diseases that the relative systematic error component of the measured voltages may be very large. Ignorance of these errors may then lead to enormous artifacts in reconstructed EIT images, which makes medical interpretation impossible.

The adaptation of the reconstruction is usually applied when measurements containing great errors occur in applications in which these are expected. If, for example, a mean value of 100 measurements shall be formed and measurement 33 is known to have been a "measuring error," this is discarded and the mean value is formed from the remaining 99 measurements. However, no such adaptation of the reconstruction rule has hitherto been performed in EIT. A full data set of all measuring channels is assumed in all reconstructions published so far, and the SNR is taken into account at best by weighting on the basis of the statistical measuring error via the correlation matrix, and systematic measuring errors are ignored by the current reconstruction rules in EIT.

SUMMARY OF THE INVENTION

An object is therefore to develop an EIT device with a process for continuous adaptation of the reconstruction rule to statistical and/or systematic measuring interferences. This EIT system must analyze the measured data of all channels for possible measuring errors continuously and, if necessary, adapt the reconstruction rule to the particular error situation in order to guarantee reconstruction that is free from interferences and artifacts as much as possible and thus clinically interpretable EIT images over the entire measuring time. In addition, the user should be informed of the measuring situation. In particular, the user should be informed in case of interferences that cannot be corrected that the EIT measurements cannot be clinically assessed.

According to the invention, an electrical impedance tomography device is provided with: a plurality of electrodes, which can be placed on a body, with control and measuring circuits to feed alternating current or alternating voltage to the electrodes and to receive voltage or current signals received from the electrodes as measured signals, and with a control unit. The control unit is connected to the control and measuring circuits and is set up by suitable programming to supply an electrode pair each with an alternating current or with an alternating voltage, to receive the voltage signal or current signal of each electrode pair from all other electrode pairs as a measured signal of a measuring channel, and to change the feeding electrode pair—have the feeding electrode pair successively run through the plurality of electrodes in order to thus receive and to process measured signals ($U_1, \ldots, U_M$) in order to reconstruct therefrom the impedance distribution of the body with a reconstruction algorithm. The control unit is set up, furthermore, by suitable programming to continuously determine at least one property ($e_1, \ldots, e_M$) each from the measured signals ($U_1, \ldots, U_M$) of all measuring channels and to correct measured signals of the measuring channels on the basis of the properties or to adapt the reconstruction algorithm on the basis of the properties.

According to another aspect of the invention, a process is provided for analyzing measured signals of an electrical impedance tomography device, which has a plurality of electrodes, which can be applied to a body, and control and measuring circuits to feed alternating current or alternating voltage to the electrodes and to receive voltage or current signals received from the electrodes. The process provides a control unit, which is connected to the control and measuring circuits and is set up by suitable programming to supply one electrode pair each with an alternating current or with an alternating voltage, to receive the voltage signal or current signal as a measured signal of each electrode pair from all other electrode pairs as a measured signal of a measuring channel and to have the feeding electrode pair successively pass through the plurality of electrodes in order to thus receive measured signals ($U_1, \ldots, U_M$) in a number of M measuring channels ($K_1, \ldots, K_M$) and to process, in order to reconstruct therefrom the impedance distribution of the body in the electrode plane with a reconstruction algorithm. The process further continuously determines at least one property ($e_1, \ldots, e_M$) from the measured signals of all measured channels and measured signals of the measuring channels are corrected on the basis of the properties or the reconstruction algorithm is adapted on the basis of the properties.

The present invention pertains to an EIT device, in which a process for continuous adaptation of the reconstruction rule and/or of the measured signals to measuring interferences of both a statistical and especially also systematic nature is implemented. The measured data of all channels are analyzed continuously for possible measuring errors and, if necessary, the reconstruction rule is adapted to the particular error situation, whereby EIT images that are free from interferences or artifacts to the greatest extent possible are guaranteed over the entire measuring time. The user is informed of the quality of the measured data by the graphic and/or alphanumeric representation of a quality index. In particular, the user should be informed in case of interferences that cannot be corrected that the EIT measurements cannot be clinically assessed. Episodes of EIT image sequences that contain errors and cannot be corrected and/or of curves of EIT data over shorter time periods and/or of trend graphs over longer periods are marked separately in the display and do not participate in the scaling of corresponding display elements.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 2:
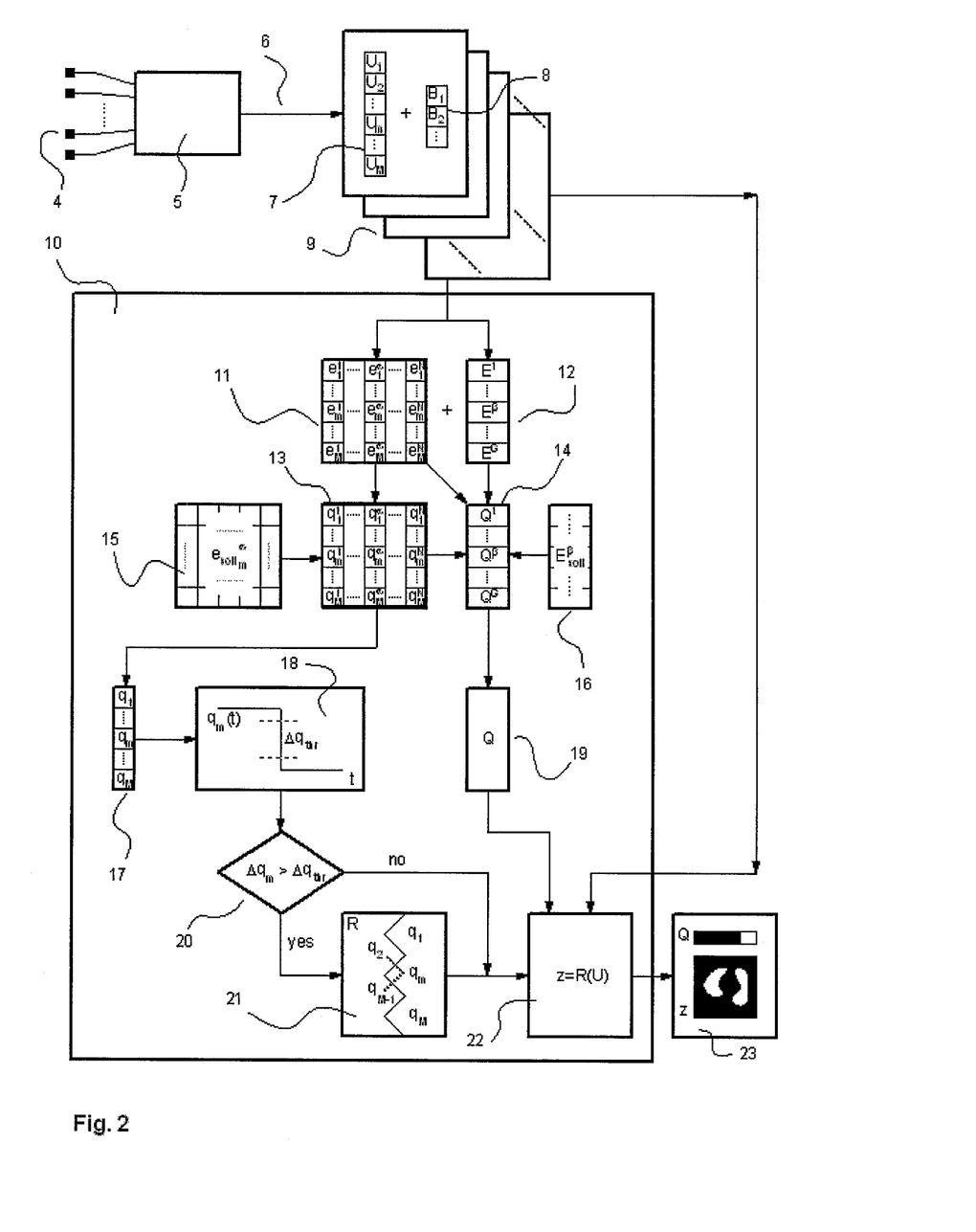
FIG. 2 is a schematic view of the EIT device with the process for adaptation of the EIT reconstruction to faulty data.
Figure 3:
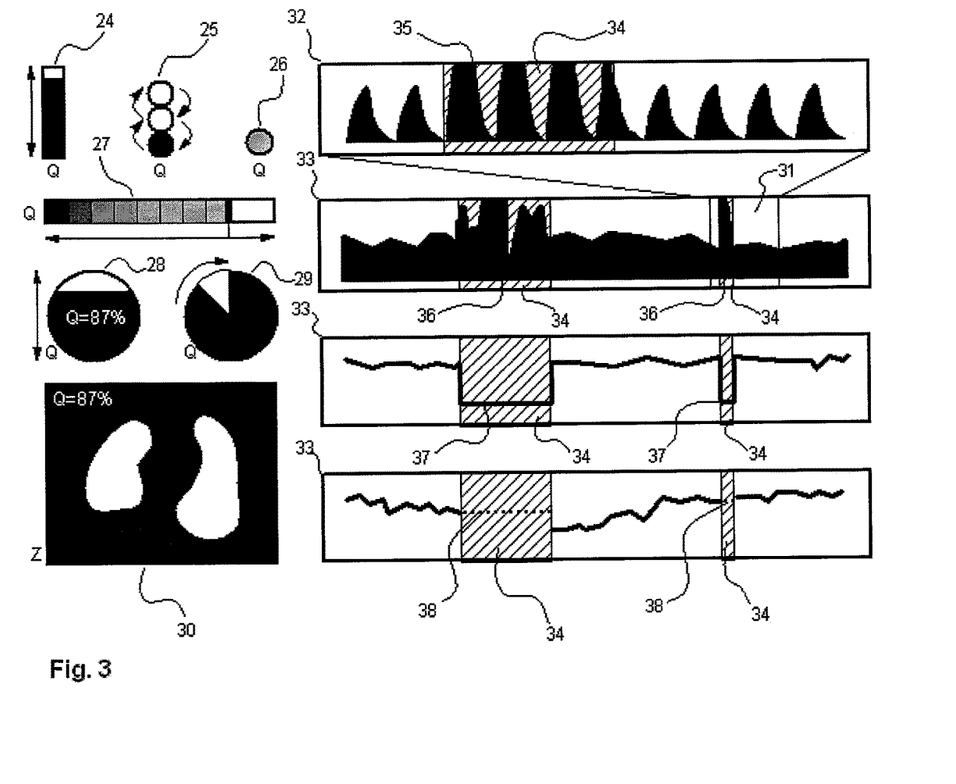
FIG. 3 is a schematic view of display elements of EIT images and curves/trends derived from EIT data with corresponding data quality information.

Referring to the drawings in particular, the present invention creates an EIT device and process with the following design features, corresponding to FIG. 2 and FIG. 3:

1. The voltages (7) of all M measuring channels are analyzed continuously for possible interferences. This can be done by comparing $\alpha = 1 \ldots N$ properties $e_m^\alpha(U_m)$ (11), the measured voltages of all m=1 ... M channels relative to expected desired values and/or desired ranges $e_{soll_m}^\alpha$ (15). The desired range can be derived, for example, from device parameters and/or from theoretical considerations such as reciprocity and/or by analyzing a large data set of EIT measurements from hospitals and/or laboratory tests with specific interferences. Examples of measurable and derivable properties of measured voltages are, of course, the SNR determined, on the one hand, but also freak values of voltages or changes of these voltages, mean value, phase and real and imaginary part of the voltage, determined crosstalk estimates of measured voltages, determined common mode estimates of voltages, reciprocity of measured voltages, voltage drifts, fluctuations in current feed, correlations between reciprocal voltage time series over a certain period, correlations between voltage and ventilation data is present, the amount and phase of the electrode skin contact impedances, characteristic properties of the value and phase distributions of the frequency spectra of the measurement series of individual channels over a certain period, e.g., maximum, standard deviation, shape of the spectral distributions, etc. It should be noted that the N properties of the measurements do not necessarily have to be independent from each other. Systematic interferences, e.g., common mode interferences or crosstalk, may be reflected in several properties, but they do not have to be.

2. An adaptation method is to determine the systematic error components of the M voltages from the N properties and to directly correct the voltages.

Figure 6:
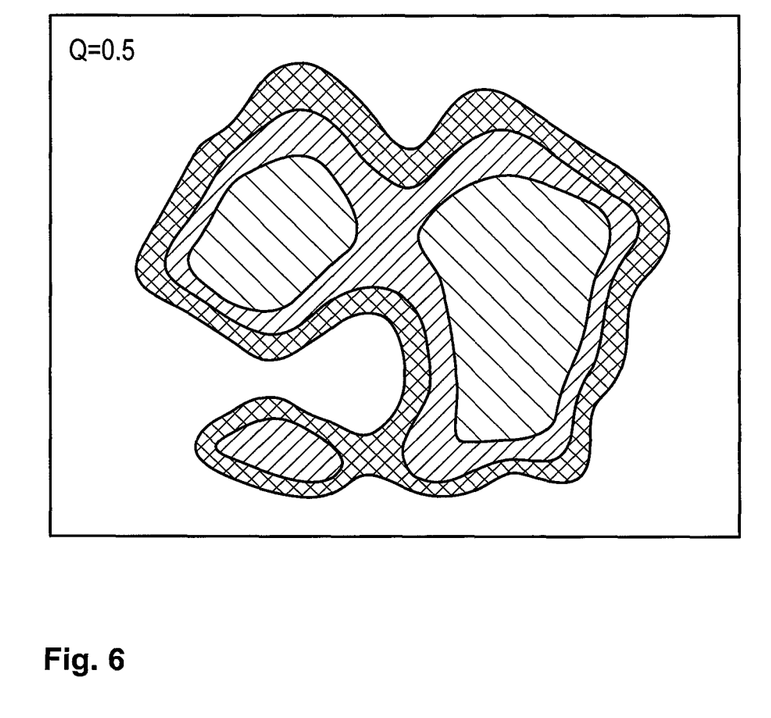
FIG. 6 is a tidal image without artifact generated from the same data set as for FIG. 4, but with adaptation to the predominantly systematic measuring errors that have occurred.

3. Another adaptation method is the channel-specific adaptation of the reconstruction rule. Channel-specific and property-specific parameters $q_m^\alpha(e_m^\alpha, e_{soll_m}^\alpha)$ (13), which can be combined into a channel-specific parameter $q_m(q_1^1, \ldots, q_m^\alpha, \ldots, q_M^N)$ (17), for example, by arithmetic or geometric means or variables derived therefrom or even combinations of different channels, are determined from the comparison of the $\alpha = 1 \ldots N$ determined properties $e_m^\alpha$ of each channel m=1 ... M with desired values $e_{soll_m}^\alpha$ derived empirically and/or theoretically beforehand. The channel-specific quality parameters are used by the reconstruction rule for the algorithmic suppression of the error-containing voltage of channel m (21). Without limitation of the general nature, the channel-specific parameters can be imaged onto a closed value range of, for example, [0,1], where measurements containing great errors can be assigned to the value 0 and measurements containing hardly any errors or even intermediate values can be assigned to q=1. Thus, channels with $q_m = 0$ could be suppressed during the EIT reconstruction (22) completely, channels with $0 < q_m < 1$ could be suppressed partly, and channels with $q_m = 1$ could not be suppressed at all. However, threshold ranges for suppression strengths can be used just as well. The concrete form in which the suppression is performed depends on the concrete reconstruction rule. One method is, for example, weighting, as it is frequently used for statistical measuring errors. The consequence of this method is that any interferences in the voltage measurements, which would become noticeable as artifacts in the EIT image without processing (FIG. 4), are markedly suppressed (FIG. 6).

4. Part of the process is the continuous, constant determination of the properties $e_m^\alpha$, as well as of the property quality parameters $q_m^\alpha(e_m^\alpha, e_{soll\ m}^\alpha)$ derived therefrom and/or of combined channel-specific quality parameters $q_m(q_1^1, \ldots q_m^\alpha, \ldots, q_M^N)$, typically over a time window. If at least one parameter changes over a certain quality parameter range $\Delta q_{thr}$ (20), the channel-specific quality parameters are used for adaptation of the reconstruction rule as described in point 2 (21). The threshold $\Delta q_{thr}$ may be, depending on the concrete implementation of the process, between one value for each channel, which has proved to be advantageous, or a plurality of values for different channels, up to the definition of a threshold for each channel m and each property $\alpha$. It is also possible to adapt the reconstruction rule for each frame.

5. Part of the process is the determination of $\beta=1 \ldots G$ of global properties $E^\beta$ (12) from measurements and/or technical operating variables. Examples of this are maxima or minima or mean values, variations or combinations of different methods of the channel-specific properties $e_m^\alpha$ and/or channel-specific quality parameters $q_m^\alpha$ and $q_m$ and/or operating current intensities, gain factors, dynamic range of the voltages, operating frequencies, norm of differential images with and without adaptation of the reconstruction rule, etc. The global properties $E^\beta$ are compared analogously to the channel-specific variables with expected desired values and/or desired ranges $E_{soll}^\beta$ (16) and global quality parameters $Q^\beta(E^\beta)$ are determined (14). The desired range for the global properties can be derived here as well, for example, from device parameters and/or from theoretical considerations and/or by analysis of a large data set, of EIT measurements from hospitals and/or laboratory tests with specific interferences. The global quality parameters $Q^\beta(E^\beta)$ are combined into a global quality index $Q(Q^1, \ldots, Q^G)$ (19), for example, by arithmetic or geometric means. The global quality index can be imaged, without limitation of the general nature, to a closed interval, for example, [0,1]. The global quality index is used for the quality classification of the EIT measurement. The quality classification may be carried out continuously or also discretely by classification into L classes, for example, good, medium, poor (L=3) or 1, 2, 3, 4, 5 (L=5), and the division of the Q interval does not have to be, in general, equidistant and is typically substantiated empirically.

6. The global quality index is displayed for the user on the display in a graphic form, e.g., by bar display (24), filling level display (28) or pie chart display (29) and/or in a color-coded manner, e.g., by traffic light type display (25), color light display (26), color-coded graphs (27) and/or in an alphanumeric manner, e.g., in percentage (30) or in any interval including improper limits a, b and/or combinations of alphanumeric and graphic display (28).

7. Episodes of poor quality (which cannot be clinically interpreted) and episodes of good quality (which can be clinically interpreted) are marked differently (34) in a trend graph of EIT variables over longer time periods (33) or curves over shorter time periods (32), for example, the summed-up impedance changes (global curve) or impedance changes summed up over ROIs (regions of interest) or time series derived from EIT data and/or from voltage data and/or from operating data.

8. Episodes of EIT images, curves, trend values with poor data quality do not participate in the scaling of the display (35), (36).

9. EIT images, curve values, trend values of episodes with poor data quality can be set at a defined value, which may be located both within the value range of their graph and outside the value range of their graph (37).

10. EIT images, curve values, trend values of episodes with poor data quality can be interpolated, and at least one EIT image or value of the curve or trend before the episode with poor data quality is used for the interpolation (38). The interpolation is likewise marked separately.

11. In case of poor data quality, a cause of error analysis (root cause analysis, RCA, in English) is performed, and possible causes of a case of error are displayed for the user. Furthermore, possibilities for eliminating the causes of error are displayed, which may lead to an improvement of the quality of measurement after an influence is exerted by the user, which makes possible a renewed interpretability of the EIT data.

The present invention will be explained in more detail below on the basis of an exemplary embodiment in connection with the figures.

FIG. 3 schematically shows some examples of display elements of EIT data with quality information. A bar graph (24) of any orientation can be represented in one color or in a color-coded manner, where a solid bar represents good quality and an empty bar poor quality or also the other way around, depending on the definition of solid and empty. The color of the bar may also change in certain cases in which a threshold value is exceeded (e.g., for good=green, medium=yellow, poor=red). A traffic light type display (25) (poor quality=red, medium quality=yellow, good quality=green) would be possible as well. Alternative codes and/or numbers of traffic lights are, of course, conceivable as well. Another display variant is, for example, a filling level display (28) or pie chart graph (29), optionally in one color or in a color-coded manner. Alphanumeric values could be present, e.g., directly in the EIT images (30) or images derived from EIT data or in/in case of graphic representations, e.g., within a filling level display (28). Trend graphs shall be defined here as graphs of EIT-based data over longer periods of time, e.g., several minutes to hours (33) under curves of rather rapidly varying variables in the range of seconds or a few minutes (32). Episodes whose data quality is so poor that the results of the reconstruction contain or can contain great errors despite adaptation processes are marked separately (34). The reconstructed values of, e.g., impedance curves (32) of the section with poor data quality are not used for scaling the display (35). This also applies to the trend graph (33) of the, e.g., end-inspiratory impedance changes (tidal strokes). The values of the tidal strokes (36), which probably contain great errors, in the marked episode with poor data quality (34) likewise do not participate in the scaling. It is also possible to set the values at a fixed value (37) or to interpolate them (34) in the trend graphs (33) of EIT-based variables in the episodes with poor data quality (34).

The following example offers a more detailed explanation of the process for the determination of the channel-specific quality indices and of the global quality parameters as well as adaptation of the reconstruction rule for this example. Variations of this example generate similar results. The following channel-specific properties were used here for a 16-electrode EIT system with 208 measuring channels in the adjacent DAQ mode:

$e_m^1$ Real part $Re(U_m)$, m=1 \ldots 208, of the voltages $U_m$ averaged over a fixed time window. The time window equals about 30 sec and contains a plurality of breaths, $e_m^2$ Phase $\phi_m = a\tan(U_m)/Re(U_m))$, m=1 \ldots 208, of the voltages $U_m$ averaged over a fixed time window, $e_m^3$ Value of the maximum voltage $\max(U_m)$, m=1 \ldots 208, of the voltages $U_m$ averaged over a fixed time window, $e_m^4$ Relative common mode errors $\Delta U_m^{\alpha_{cm}} = |\Delta U_m^{cm}|/|U_m|$, m=1 \ldots 208, of the voltages $U_m$ averaged over a fixed time window, wherein the common mode error $\Delta U_m^{cm}$ can be determined from special measurements as a function of the specific hardware embodiment and model hypotheses following therefrom, $e_m^5$ Reciprocity $r_m=|(|U_m|-|U_{m'}|)/(|U_m|+|U_{m'}|)|$, m, m'=1 ... 208, of the respective voltages $U_m$ and $U_{m'}$, wherein m, m' are mutually reciprocal channels. $r_m=r_{m'}$ applies.

$e_m^6$ Signal-to-noise ratio $SNR_m=20 \log_{10}(U_m/N_m)$, m=1 ... 208. the channel-specific noise component $N_m$ was estimated from the effective value of a high pass-filtered voltage time series with a limit frequency above the frequency range of the physiological signal sources (ventilation, heart beat).

The property-specific quality index $q_m^\alpha$ was determined from the following calculation instruction.

$$q_m^\alpha(e_m^\alpha, c_m^\alpha, d_m^\alpha) = \begin{cases} 1, & 1+\frac{c_m^\alpha - e_m^\alpha}{d_m^\alpha \cdot c_m^\alpha} > 1 \\ 1+\frac{c_m^\alpha - e_m^\alpha}{d_m^\alpha \cdot c_m^\alpha}, & 0 \leq 1+\frac{c_m^\alpha - e_m^\alpha}{d_m^\alpha \cdot c_m^\alpha} \leq 1 \\ 0, & 1+\frac{c_m^\alpha - e_m^\alpha}{d_m^\alpha \cdot c_m^\alpha} < 0 \end{cases}$$

Figure 7A:
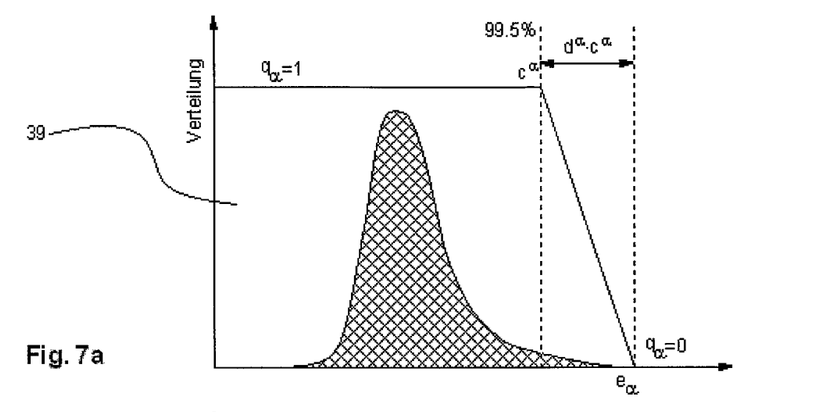
FIG. 7a is a schematic views of the probability distributions of the measuring channel properties $e^\alpha$ (for all m or a subset of m), determined from a representative set of clinical data, as well as a simple functional relationship $q_m^\alpha(e_m^\alpha, e_{soll_m}^\alpha)$ between the quality indices and measured properties with $q_m^\alpha = 1$
for $e_m^\alpha < e_{soll_m}^{\alpha_1}$, $q_m^\alpha = 0$
for $e_m^\alpha > e_{soll_m}^{\alpha_2}$,
linear drop for $e_{soll_m}^{\alpha_1} \le e_m^\alpha \le e_{soll_m}^{\alpha_2}$.
Figure 7B:
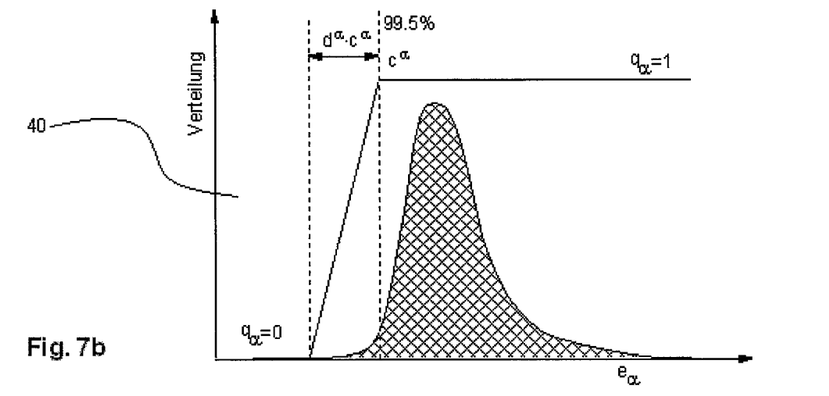
FIG. 7b is a schematic views of the probability distributions of the measuring channel properties $e^\alpha$ (for all m or a subset of m), determined from a representative set of clinical data, as well as a simple functional relationship $q_m^\alpha(e_m^\alpha, e_{soll_m}^\alpha)$
between the quality indices and measured properties with $q_m^\alpha = 1$
for $e_m^\alpha > e_{soll_m}^{\alpha_1}$, $q_m^\alpha = 0$
for $e_m^\alpha < e_{soll_m}^{\alpha_2}$,
linear drop for $e_{soll_m}^{\alpha_1} \ge e_m^\alpha \ge e_{soll_m}^{\alpha_2}$.
Figure 7C:
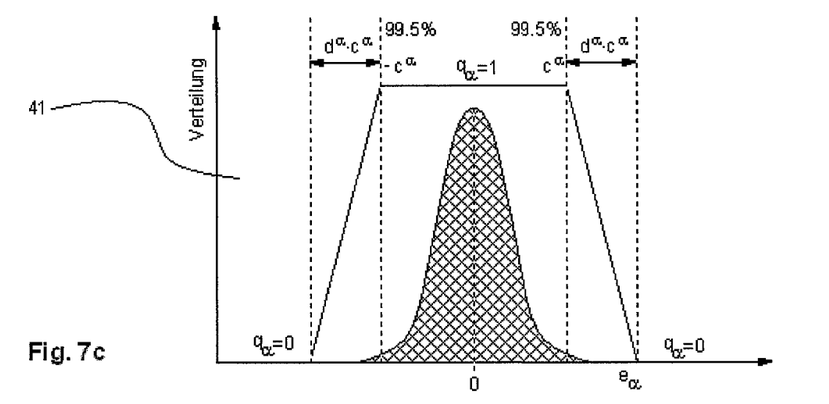
FIG. 7c is a schematic views of the probability distributions of the measuring channel properties $e^\alpha$ (for all m or a subset of m), determined from a representative set of clinical data, as well as a simple functional relationship $q_m^\alpha(e_m^\alpha, e_{soll_m}^\alpha)$
between the quality indices and measured properties with $q_m^\alpha = 1$
for $|e_m^\alpha| < e_{soll_m}^{\alpha_1}$, $q_m^\alpha = 0$ for,
for $|e_m^\alpha| > e_{soll_m}^{\alpha_2}$,
linear drop for $e_{soll_m}^{\alpha_1} \le |e_m^\alpha| \le e_{soll_m}^{\alpha_2}$.

As a variation of this instruction, a hysteresis threshold may also be agreed upon, or other, more complex variants. This depends on the particular hardware and also on the experience with the behavior of clinical data. To determine the slice parameters $c_m^\alpha$, $d_m^\alpha$, more than 400 data sets from clinical studies were analyzed. Distributions were determined for all properties $e_m^\alpha$; they are schematically shown in FIGS. 7a)-7c).

It was specified that a slice $c_m^\alpha$ each is set at a value $e_m^\alpha$, where 99.5% of the data are below (FIG. 7a, e.g., reciprocity) or above (FIG. 7b, e.g., real part of the voltage) or in a range (FIG. 7c, e.g., phase), depending on which range is considered to increasingly contain systematic error. For example, the reciprocity is mentioned for the distribution type in FIG. 7a). It is ideally 0; excessively high values are indicative of systematic measuring errors, and the slice is therefore at the upper end. For example, the real part of the voltage shall be mentioned for distribution type 7b. The greater this is, the more unlikely is a high component of systematic error, and therefore the slice is for excessively low values. The phase shall be mentioned for distribution type 7c). They are scattered around a mean value, which depends mainly on the current feed frequency used, the average electrode-skin contact impedance and the analog electronic unit. Very large negative and positive phases, which are indicative of large systematic error components, may develop in case of great magnetic uncoupling or crosstalk. The decay value $d_m^\alpha$ sets the range of quality index between 0 and 1 and the hysteresis range and prevents a possible flutter, which would occur in case of properties $e_m^\alpha$ near the slice value $c_m^\alpha$ and jump function $q_m^{\alpha'}$ between 1 and 0 at the slice value. "Bootstrapping" could also be used in alternative variant of setting the slice by setting slices for properties except one and then estimating the probability distribution for systematic errors of the properties left out on the basis of the data set and determining the slices for the variable left out by means of these. This variable is then added, another one is left out, and the process is repeated until all slices are set in this manner. An iterative procedure is also possible for this. Regardless of the determination of the slices from a large set of clinical data, the concrete values of the slice parameters $c_m^\alpha$, $d_m^\alpha$ depend on how the concrete hardware of an EIT system responds to the measuring conditions in routine clinical practice.

The channel-specific quality index $q_m$ was determined here from the product of the property- and channel-specific quality indices $q_m^\alpha$:

$$q_m = \prod_{\alpha=1}^{6} q_m^\alpha$$

This is a conservative hypothesis, because even one property containing great errors may lead to great interferences in the EIT image and reduce possible correlations between different properties. In addition, the channel-specific quality index of adjacent channels m±1 of an extremely greatly disturbed channel m may conservatively also be set to 0. This was not used in this example.

Figure 5:
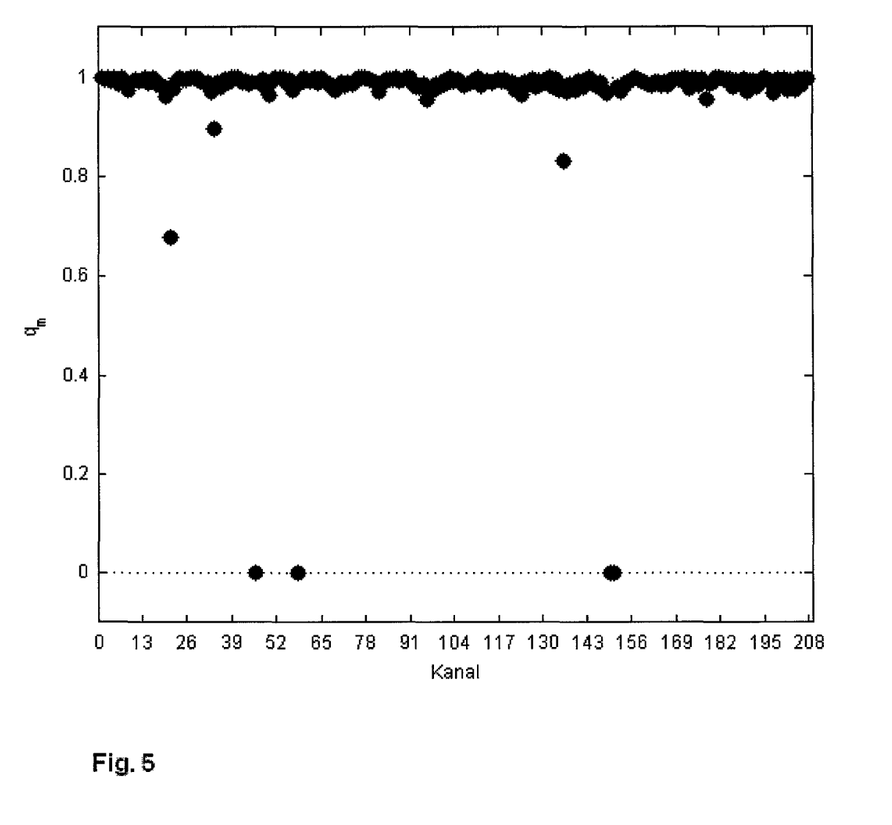
FIG. 5 is a view of the 208 channel-specific quality parameters determined.

The channel-specific data quality analysis according to process steps 1) through 3) led to the combined channel-specific quality parameter $q_m$ shown in FIG. 5. It is seen that most channels have, indeed, measured nearly error-free ($q_m$ values close to 1), three channels had moderate systematic errors, but three channels had massive systematic errors, so that the $q_m$ values of 0 were assigned to them according to the method explained in detail above. It shall be noted that no major statistical errors, i.e., noise, were present in this measurement. The SNR was in the expected range. The cause was a systematic common mode error during the voltage measurement in this case!

The channel-specific quality indices $q_m$ were used to define a systematic error weighting matrix:

$$W = \text{diag}(q_1, q_2, \ldots, q_{208}).$$

A sensitivity matrix-based Newton-Raphson method was used to reconstruct the vector $\Delta p^n$ of the relative impedance change from the relative voltage change $\Delta u^n$. Sensitivity matrix S was determined from a finite element model of the thorax using the linearized Geselowits relation. The adaptation of the reconstruction matrix A to the concrete systematic errors found was performed by integrating the systematic error weighting matrix W in the determination of the reconstruction matrix:

$$A = R(S^T W S + \lambda L^T L)^{-1} S^T W, \Delta p^n(t) = A \Delta u^n(t).$$

Matrix L designates the regularization matrix, the scalar variable $\lambda$ designates the regularization parameter, and matrix R represents a filtered registration matrix from the FEM system to the pixel system of the EIT image.

Figure 4:
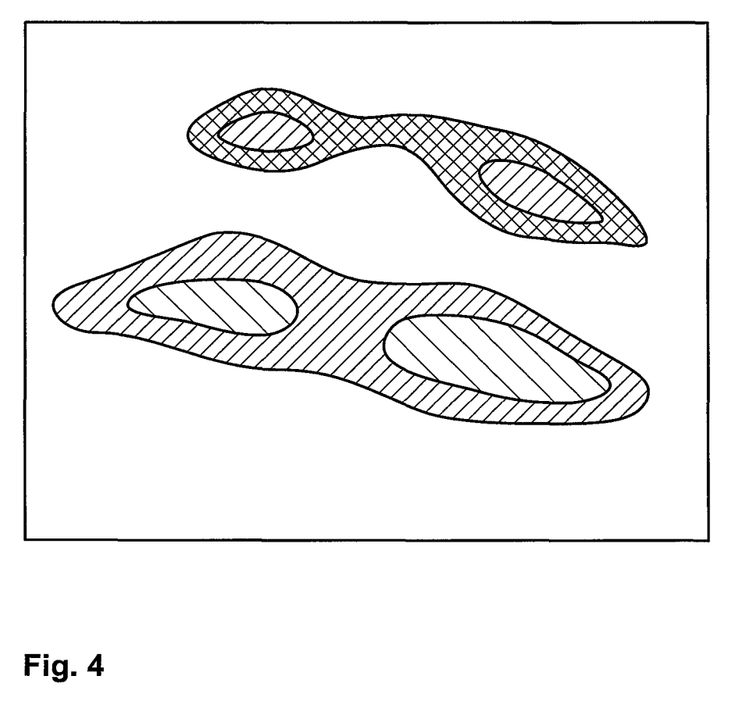
FIG. 4 is a tidal image with large artifact generated from a 30-second data sampling with a 16-electrode EIT system without adaptation to predominantly systematic measuring errors that have occurred.

In FIG. 4, we find an EIT image generated from the relative voltage changes between end-inspiratory and end-expiatory states of the lungs with a data acquisition time of about 30 sec in a hospital in the adjacent DAQ mode with an EIT system with 16 electrodes (208 channels) without the use of the above-described method of adaptation of the reconstruction rule, i.e., the above reconstruction rule was used therefor with W=I, wherein I is the 208-dimensional identity matrix here. This means as an assumption that all measuring channels are free from systematic errors, as, e.g., in the frequently used back projection. The horizontal structure shown in FIG. 4 can be primarily classified as a an artifact, which was caused by the three greatly interfered channels with $q_m$=0. The large artifact has nothing to do with the actual impedance change distribution, which is considered an indicator of the regional ventilation. A clinical assessment of this image would lead to an excessively clear misinterpretation.

In FIG. 6, we find the EIT image, which is based on the same interfered measured data as the image in FIG. 4, with applied adaptation of the reconstruction rule according to the above formula, including the quality indices in FIG. 5, which were determined from the quality analysis, in the systematic error weighting matrix W. Complete suppression of the values of the three $q_m=0$ channels cause the artifact in the EIT image in FIG. 6 to disappear. A normally ventilated left lung is found here (thoracic CT cross section convention: on the right in the figure), but also a hypoventilated right lung in the dorsal area, in agreement with clinical X-ray findings. By applying process step 4), which will be explained in more detail below for this exemplary embodiment, a global quality index of Q=0.5 was assigned, which corresponds to medium data quality, because even when the EIT data were interpreted with the use of the adaptative reconstruction method, the user should be informed that measuring errors occurred. A root cause analysis revealed large common mode components at electrode pair 11, 12 based on poor electrode-skin contact impedance of electrode 12. A suggestion to check the contact of the electrode according to process step 8 can put things right in such cases.

The systematic errors prove to be highly constant over time. A repeated adaptation is indicated above all if a quality index worsens over a large range, e.g., $\Delta q_m > 0.8$, because an already bad channel may generate a large artifact. Conversely, markedly improved channels need to be adapted in case of a larger number of markedly improved channels (greater than, e.g., 6) only, because only the accuracy is improved somewhat statistically compared to the previous solution without these channels.

The following global properties were used in this example for the determination of the global data quality index:
$E^1$: Mean value of the channel-specific quality index
$E^2$: Maximal values of the channel-specific property $e_m^6$
$E^3$: Dynamic range (ratio of maximum voltage to minimum voltage)
$E^4$: Technical operating state (flag sent by the EIT system 0 or 1).

The distributions of the global data quality parameters were determined, except for the technical operating state flag, which was provided by the device, analogously to the case of the channel-specific properties, from over 400 clinical data sets, and the slice values and decay intensities $E^\beta=(C^\beta, D^\beta)$ were determined analogously and empirically adapted in the second iteration by expert consideration of corresponding EIT images. The determination of the property-specific global data quality parameters $Q^\beta$ was performed with an analogous formula as for the channel-specific data quality parameters $q_m^\alpha$:

$$Q^\beta(E^\beta, C^\beta, D^\beta) = \begin{cases} 1, & 1+\frac{C^\beta-E^\beta}{D^\beta \cdot C^\beta} > 1 \\ 1+\frac{C^\beta-E^\beta}{D^\beta \cdot C^\beta}, & 0 \le 1+\frac{C^\beta-E^\beta}{D^\beta \cdot C^\beta} \le 1 \\ 0, & 1+\frac{C^\beta-E^\beta}{D^\beta \cdot C^\beta} < 0 \end{cases}$$

The following values were obtained: $Q^1=0.89$, $Q^2=1$, $Q^3=0.56$, $Q^4=1$. The global quality index Q was likewise determined from the product of the property-specific global quality index $Q^\beta$:

$$Q = \prod_{\beta=1}^{4} Q^\beta$$

A value, of $Q \approx 0.5$ was obtained, which is shown in the top left part of FIG. 6. This is a middle range. The user now knows that the measurement can be interpreted based on the adaptation of the reconstruction rule, but also that channels with systematic errors are present.

While specific embodiments of the invention have been shown and described in detail to illustrate the application of the principles of the invention, it will be understood that the invention may be embodied otherwise without departing from such principles.

APPENDIX

List of Reference Numbers

1 Current feed between current-carrying electrodes
2 Rotation of current feed
3 Rotation of voltage measurement per current feed position
4 Electrodes+cables for EIT measurement at the subject
5 EIT device
6 Data transport, data flow
7 Measured value vector of the voltages U of all channels of one frame
8 Vector with operating data of a frame
9 Data set from voltages and operating information from at least one frame
10 Computing unit
11 Determination of the channel-specific properties from the data set
12 Determination of the G global properties from the data set
13 Determination of the channel- and property-specific quality parameters
14 Determination of the global quality parameters of the global properties
15 Data bank or list with desired values/desired ranges of the channel-specific properties
16 Data bank or list with desired values/desired ranges of global properties
17 Determination of the channel-specific quality indices
18 Analysis of the behavior over time of the channel-specific quality indices
19 Determination of the global quality index for the measurement
20 Decision for adaptation of the reconstruction rule or further use of the current one on the basis of the changes in the channel-specific quality indices compared to desired values
21 Adaptation of the reconstruction rule with inclusion of the channel-specific quality indices
22 Reconstruction of the EIT data from the voltages of the data set
23 Display of the EIT data with quality indicator
24 Bar display of the global quality index Q
25 Traffic light type display of the global quality index Q
26 Only color- and/or brightness-coded display of the global quality index Q
27 Bar display with quasi-continuous color- and/or brightcoded display of the global quality index Q
28 Filling level display with alphanumeric value of the global quality index Q
29 Pie chart display of the global quality index Q
30 Tidal image with alphanumeric quality display
31 Short time period of a long time period in the trend graph of the tidal strokes
32 Impedance curve of the short time period (e.g., about 1 minute) with ventilation 33 Trend graphs of different EIT-derived variables over a longer time period (e.g., 10 minutes)
34 Marked episode with poor data quality (not interpretable)
35 Faulty values of the impedance curve during the episode with poor data quality (adaptation of the reconstruction was, e.g., no longer possible because of too many errors), which do not participate in the scaling of display 32 and are not therefore fully displayed
36 Faulty values for tidal strokes during the episode with poor data quality, which do not participate in the scaling
37 Setting of values of a trend graph at a preset value during an episode with poor data quality
38 Interpolation of values of a trend graph with the last value of the trend graph before the episode with poor data quality
39 Asymmetric probability distribution for a channel property $e^\alpha$, for example, reciprocity and common mode voltages (see above) with slice at excessively high values
40 Asymmetric probability distribution for a channel property $e^\alpha$, for example, real parts of the 4 lowest voltages per patient (see above) with slice at excessively low values
41 Symmetrical probability distribution for a channel property $e^\alpha$, for example, phases of the voltages with subtracted mean value or 2f distributions of modulation with slices at excessively high values

What is claimed is:

1. An electrical impedance tomography (EIT) device comprising:
   a plurality of electrodes, which can be placed on a body;
   control and measuring circuits to feed alternating current or alternating voltage to said electrodes and to receive voltage or current signals received from said electrodes as measured signals;
   a control unit connected to said control and measuring circuits and configured to control a supply of alternating current or with an alternating voltage to an electrode pair as a feeding electrode pair and configured to receive measured voltage signal or measured current signal of each electrode pair from all other electrode pairs as measured signals, and to successively change said feeding electrode pair through said plurality of electrodes and to receive and to process the measured signals ($U_1, \ldots, U_M$) of a plurality of (M) individual measuring channels ($K_1, \ldots, K_M$) and to reconstruct therefrom an impedance distribution of the body with a reconstruction algorithm, said control unit further configured to continuously determine at least one property ($e^\alpha_1, \ldots, e^\alpha_M$) of a set ($\alpha$) of properties to determine channel-specific quality parameters ($q_1, \ldots, q_M$) by a comparison of said at least one property of each channel with predetermined desired values, the properties comprising signal-to-noise ratio of the measured signals, freak value of the measured signals, mean value of the measured signals, phase or real and imaginary part of the measured signals, crosstalk of the measured signals, common mode of the measured signals reciprocity of the measured signals, measured signal drifts, current feed fluctuations, and value and phase of the electrode-skin contact impedances, each from said measured signals ($U_1, \ldots, U_M$) of all measuring channels and configured to correct measured signals of said measuring channels based on said at least one property by adapting the reconstruction algorithm based on the at least one property by including the channel-specific quality parameters ($q_1, \ldots, q_M$) among channel-specific properties in the reconstruction algorithm in a matrix that comprises a weighting matrix $W(q_1, \ldots, q_M)$ that comprises the channel-specific quality parameters ($q_1, \ldots, q_M$), wherein
   said control unit furthermore determines at least another property so as to determine N properties $e_m^\alpha(U_M)$ ($\alpha=1, \ldots, N$) of the set ($\alpha$) of properties in all measuring channels for each measured signal ($U_1, \ldots U_M$) and compares the N properties with desired values or with desired ranges $e_{soll_m}^\alpha$ determined in advance or with both the desired values and with the desired ranges determined in advance, to provide results of a comparison, and corrects the measured signals of the measuring channels based on the results of the comparison based on the properties or adapts the reconstruction algorithm based on the properties;
   said control unit determines channel-specific quality parameters and property-specific quality parameters $q_m^\alpha(e_m^\alpha, e_{soll_m}^\alpha)$ from the comparison of the determined properties $e_m^\alpha$ of each channel $m=1, \ldots, M$ with desired values or desired value ranges $e_{soll_m}^\alpha$ determined in advance, wherein the channel-specific quality parameters are included in the reconstruction algorithm in such a manner that measuring channels with channel-specific quality parameters that are indicative of signals of a lower quality relative to other signals are weighted less strongly than measuring channels with quality parameters that are indicative of signals with a higher quality relative to other signals; and
   said control unit forms each of the channel-specific quality parameters from the property-specific quality parameters $q_m^\alpha(e_m^\alpha, e_{soll_m}^\alpha)$, to provide the channel-specific quality parameters $q_m(q_m^1, \ldots, q_m^\alpha, \ldots, q_M^N)$, by arithmetic or geometric averaging of the property-specific quality parameters $q_m^\alpha(e_m^\alpha, e_{soll_m}^\alpha)$ for each measuring channel, wherein the channel-specific quality parameters are standardized for an interval, wherein the lowest quality is assigned to the value 0 and the highest quality is assigned to the value 1, and wherein the measuring channels are weighted according to this standardized quality parameter in the reconstruction algorithm.

2. An electrical impedance tomography (EIT) device in accordance with claim 1, wherein said control unit continuously updates determination of the properties $e_m^\alpha$ or the property-specific quality parameters derived therefrom or the combined channel-specific quality parameters or any combination of the properties, the property-specific quality parameters derived therefrom and the channel-specific quality parameters, wherein the determination is performed over a time window.

3. An electrical impedance tomography device according to claim 1, wherein adapting the reconstruction algorithm comprises forming an adaptation of the reconstruction matrix A with the integrated weighting matrix $W(q1, \ldots, qM)$ that comprises the channel-specific quality parameters ($q1, \ldots, qM$), wherein:
   a sensitivity matrix-based Newton-Raphson method is used to reconstruct a vector $\Delta p''$ of the relative impedance change from the relative voltage change $\Delta u''$, with $\Delta p''(t) = A\Delta u''(t)$;
   the adaptation of the reconstruction matrix A is in the form:
   $A = R(S^T W S + \lambda L^T L)^{-1} S^T W$, and the sensitivity matrix S is determined from a finite element model (FEM) using the linearized Geselowits relation, the matrix L designates a regularization matrix, the scalar variable $\lambda$ designates a regularization parameter, and matrix R represents a filtered registration matrix from the FEM system to the pixel system of the EIT image.

4. An electrical impedance tomography (EIT) device in accordance with claim 1, wherein said control unit continuously determines a plurality of global properties $E^\beta$, $\beta=1 \ldots G$ from the measured signals of the measuring channels, or from properties thereof or from technical operating variables of the electrical impedance tomography device or from any combination of the measured signals of the measuring channels, from properties thereof and from technical operating variables of the electrical impedance tomography device, wherein the global properties are at least one of the properties selected from the group of properties that include maxima, minima or mean values or combinations of the properties $e_m^\alpha$ and of the channel-specific quality parameters $q_m^\alpha$ and operating current intensities, gain factors, dynamic range of the measured signals, operating frequencies, and the standard of differential EIT images with and without adaptation of the reconstruction algorithm, wherein the control unit furthermore compares the global properties $E^\beta$ with expected desired values or desired value ranges $E_{soll}^\beta$, or with both expected desired values and desired value ranges, to provide results of a comparison and determines global quality parameters $Q^\beta$ ($E^\beta$) based on of the results of the comparison.

5. An electrical impedance tomography (EIT) device in accordance with claim 4, wherein said control unit combines the global quality parameters $Q^\beta$ ($E^\beta$) into a global quality index $Q(Q^1, \ldots, Q^G)$, by arithmetic or geometric averaging of the global quality parameters, wherein the control unit standardizes the global quality index to an interval and uses the global quality index for the quality classification of the EIT measurements.

6. An electrical impedance tomography (EIT) device in accordance with claim 5, wherein said control unit displays the global quality index graphically or alphanumerically on a display.

7. An electrical impedance tomography (EIT) device in accordance with claim 5, wherein said control unit marks time intervals separately in which the quality index is below a preset minimum criterion for derived variables, which variables are derived from the measured impedance distribution, and which have a development course over time shown on a display, and replaces values for the time analysis of the values with values derived from adjacent intervals, by interpolation or averaging, or with preset values to provide replaced time intervals, wherein the replaced time intervals are marked separately.

8. A process for analyzing measured signals of an electrical impedance tomography (EIT) device, the process comprising:
providing a plurality of electrodes, which can be applied to a body, control and measuring circuits to feed alternating current or alternating voltage to the electrodes and to receive voltage or current signals received from the electrodes;
connecting a control unit to the control and measuring circuits;
supplying one electrode pair, as a feeding electrode pair, with an alternating current or with an alternating voltage with the control unit;
receiving the measured voltage signal or measured current signal as a measured signal of each electrode pair from all other electrode pairs as measured signals;
changing the feeding electrode pair successively to pass through the plurality of electrodes and receive measured signals ($U_1, \ldots, U_M$) in a number of M measuring channels ($K_1, \ldots, K_M$);
processing the received measured signals ($U_1, \ldots, U_M$) in the number of M measuring channels ($K_1, \ldots, K_M$) including reconstructing therefrom an impedance distribution of the body in an electrode plane, of the plurality of electrodes, with a reconstruction algorithm with the control unit;
continuously determining, with the control unit, at least one property ($e_1, \ldots, e_M$) of a set ($\alpha$) of properties comprising signal-to-noise ratio of the measured signals, freak value of of the measured signals mean value of the measured signals, phase or real and imaginary part of the measured signals, crosstalk of the measured signals common mode of the measured signals reciprocity of the measured signals, measured signal drifts, current feed fluctuations, and value and phase of the electrode-skin contact impedances, of all measured signals of all measuring channels;
determining, with the control unit, channel-specific quality parameters ($q_1, \ldots, q_M$) by a comparison of said at least one property of each channel with predetermined desired values;
and
correcting measured signals of said measuring channels based on said at least one property by adapting the reconstruction algorithm based on the at least one property by including the channel-specific quality parameters ($q_1, \ldots, q_M$) among channel-specific properties in the reconstruction algorithm in a matrix that comprises a weighting matrix $W(q_1, \ldots, q_M)$ that comprises the channel-specific quality parameters ($q_1, \ldots, q_M$), wherein
the control unit determines at least another property so as to determine N properties $e_m^\alpha(U_M)$ ($\alpha=1, \ldots, N$) in all measuring channels for each measured signal ($U_1, \ldots U_M$), and compares the determined N properties with desired values or desired ranges $e_{soll_m}^\alpha$ determined in advance or both desired values and desired ranges determined in advance to provide results of a comparison, and corrects the measured signals of the measuring channels based on the results of the comparison based on the properties or to adapt the reconstruction algorithm based on the properties;
said control unit determines channel-specific quality parameters and property-specific quality parameters $q_m^\alpha(e_m^\alpha, e_{soll_m}^\alpha)$ from the comparison of the determined properties $e_m^\alpha$ of each channel $m=1, \ldots, M$ with desired values or desired value ranges $e_{soll_m}^\alpha$ determined in advance, wherein the channel-specific quality parameters are included in the reconstruction algorithm in such a manner that measuring channels with quality parameters that are indicative of signals of a lower quality relative to other signals are weighted less strongly than measuring channels with quality parameters that are indicative of signals with a higher quality relative to other signals; and
said control unit forms each of the channel-specific quality parameters from the property-specific quality parameters $q_m^\alpha(e_m^\alpha, e_{soll_m}^\alpha)$, to provide the channel-specific quality parameters $q_m(q_1^1, \ldots, q_m^\alpha, \ldots, q_M^N)$, by arithmetic or geometric averaging of the property-specific quality parameters $q_m^\alpha(e_m^\alpha, e_{soll_m}^\alpha)$ for each measuring channel, wherein the channel-specific quality parameters are standardized for an interval, wherein the lowest quality is assigned to the value 0 and the highest quality is assigned to the value 1, and wherein the measuring channels are weighted according to this standardized quality parameter in the reconstruction algorithm.

9. A process for analyzing measured signals of an electrical impedance tomography (EIT) device in accordance with claim 8, wherein said control unit continuously updates a determination of the properties $e_m^\alpha$ or the property quality parameters derived therefrom or the combined channel-specific quality parameters or any combination of the determination of the properties and the property quality parameters derived therefrom and the combined channel-specific quality parameters, wherein the determination is performed over a time window.

10. A process for analyzing measured signals of an electrical impedance tomography (EIT) device in accordance with claim 8, wherein said control unit continuously determines a plurality of global properties $E^\beta$, $\beta=1\ldots G$ from at least one of the properties of the group of properties comprising the measured signals of the measuring channels, from properties thereof and from technical operating variables of the electrical impedance tomography device or from any combination of the measured signals of the measuring channels, from properties thereof and from technical operating variables of the electrical impedance tomography device, wherein the global properties are at least one of the properties selected from the group of properties that include maxima, minima or mean values or combinations of the channel-specific properties $e_m^\alpha$ and the channel-specific quality parameters $q_m^\alpha$ and operating current intensities, gain factors, dynamic range of the measured signals, operating frequencies, and the standard of differential EIT images with and without adaptation of the reconstruction algorithm, wherein the control unit compares the global properties $E^\beta$ with expected desired values or desired value ranges $E_{soll}^\beta$ or with both expected desired values and desired value ranges to provide results of a comparison and determines global quality parameters $Q^\beta(E^\beta)$ on the basis of the results of the comparison.

11. A process for analyzing measured signals of an electrical impedance tomography (EIT) device in accordance with claim 10, wherein said control unit combines the global quality parameters $Q^\beta(E^\beta)$ into a global quality index $Q(Q^1, \ldots, Q^G)$, by arithmetic or geometric averaging of the global quality parameters, wherein the control unit standardizes the global quality index to an interval and uses the global quality index for the quality classification of the EIT measurements.

12. A process for analyzing measured signals of an electrical impedance tomography (EIT) device in accordance with claim 11, wherein said control unit displays the global quality index graphically or alphanumerically on a display.

13. A process for analyzing measured signals of an electrical impedance tomography (EIT) device in accordance with claim 11, wherein said control unit marks time intervals separately in which the quality index is below a preset minimum criterion for derived variables, which variables are derived from the measured impedance distribution, and which have a development course over time shown on a display, and replaces values for the time analysis of the values with values derived from adjacent intervals, by interpolation or averaging, or with preset values to provide replaced time intervals, wherein the replaced time intervals are marked separately.

* * * * *